United States Patent [19]

Glaser

[11] 4,039,942
[45] Aug. 2, 1977

[54] SYSTEM FOR SENSING ELECTRICAL POTENTIAL PARTICULARLY IN PLANTS

[76] Inventor: David Glaser, c/o E. H. Rainer, 3400 Virginia Road, Cleveland, Ohio 44122

[21] Appl. No.: 602,113

[22] Filed: Aug. 5, 1975

[51] Int. Cl.² .......................................... G01R 31/02
[52] U.S. Cl. .................................. 324/72; 324/65 R; 324/133; 324/123 C; 307/237
[58] Field of Search ..................... 324/72, 72.5, 123 C, 324/133, 65 R; 128/2 E, 2.06 E, 2.1 E; 328/54, 142, 143, 169, 171; 307/237

[56] References Cited

U.S. PATENT DOCUMENTS

| | | | |
|---|---|---|---|
| 3,659,213 | 4/1972 | Platt | 307/237 |
| 3,688,309 | 8/1972 | Volberg | 324/65 R |
| 3,699,562 | 10/1972 | Kelly | 324/133 |
| 3,873,919 | 3/1975 | Vosteen | 324/123 C |
| 3,901,218 | 8/1975 | Buchalter | 128/2.06 E |

OTHER PUBLICATIONS

Lawrence, "Electronics and the Living Plant," Electronics World, Oct., 1969, pp.25-28.

Primary Examiner—Rudolph V. Rolinec
Assistant Examiner—Michael J. Tokar
Attorney, Agent, or Firm—Marvin Reich

[57] ABSTRACT

The system includes two conductive sensors to be placed in contact with a body which exhibits voltage changes, such as the leaves of a plant. The sensors are connected to an amplifier having high input impedance and connected with positive feedback and providing good common mode rejection. The amplifier output, in response to voltage changes sensed by the sensors, drives a coil having an iron core, and current flow through the coil is sensed by a utilization device, which, in one arrangement, comprises a magnet secured to the clapper of wind bells.

6 Claims, 3 Drawing Figures

SYSTEM FOR SENSING ELECTRICAL POTENTIAL PARTICULARLY IN PLANTS

BACKGROUND OF THE INVENTION

It has long been known that the leaves of plants exhibit changes in electrical potential, and prior art systems are known for sensing and representing these voltage changes. However, those known systems are complex and expensive, at least in part, because they require complex electrical shielding arrangements and means for making electrical contact to the leaves.

DESCRIPTION OF THE PREFERRED EMBODIMENTS

Figure 1:
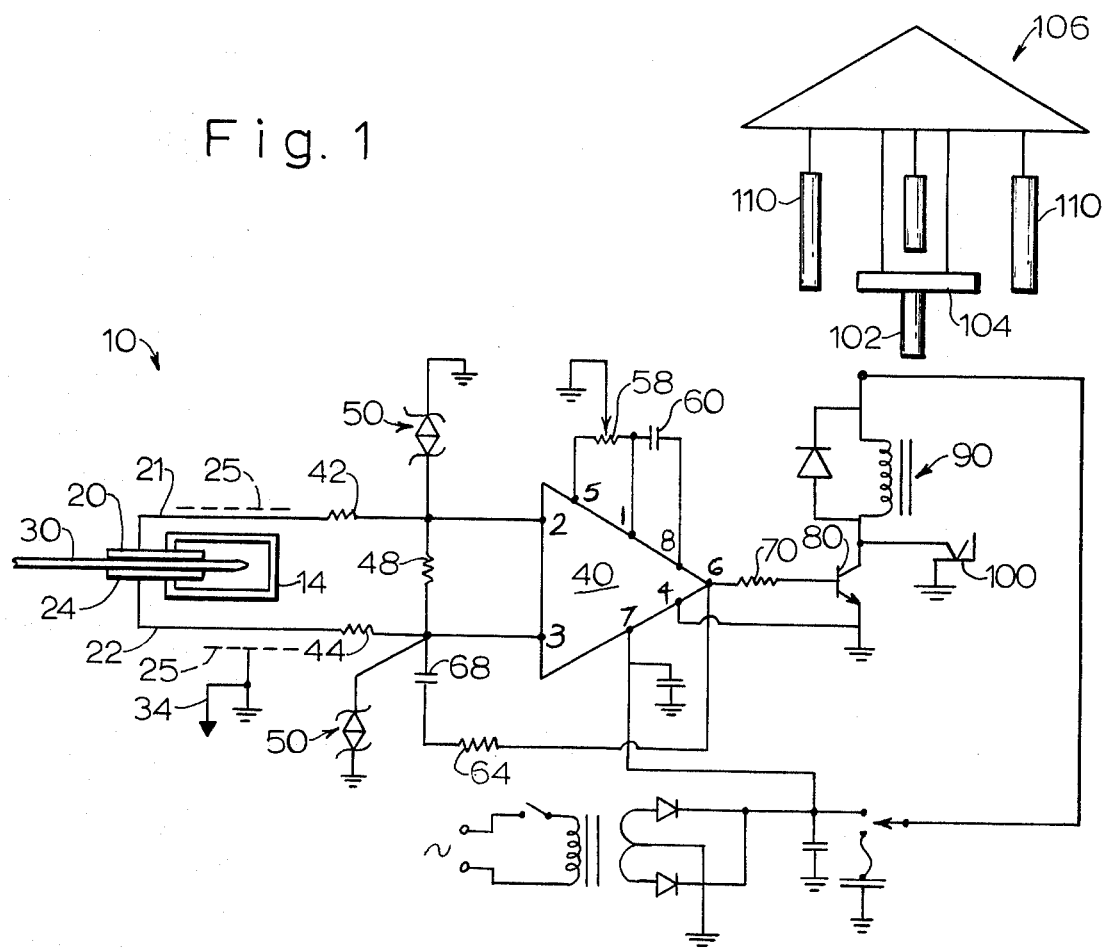
FIG. 1 is a schematic representation of the system of the invention.

A system 10 embodying the invention includes a pair of electrical sensors 20 and 24 which are placed in contact with a body 30 whose electrical potential is to be sensed. In one specific use of the system, the body is a plant leaf. For use with a plant leaf, the sensors are pads of conductive polyurethane carried by a suitable clamping arrangement 14, by which the sensors are clamped to the leaf 30. A reference probe 34, which may comprise a metal pin, is coupled to the leads from the sensors 20 and 24. Leads 21 and 22 are preferably shielded cable, and probe 34 is connected to the shield as represented by dash lines 25.

The system 10 preferably utilizes a COS/MOS operational amplifier 40, such as the RCA 3130 linear integrated circuit amplifier (FIG. 2), which has a very high input impedance of about $1.5 \times 10^{12}$ ohms. The amplifier 40 is preferably one of high sensitivity and has two input terminals, carrying numerals 2 and 3, terminal 2 being connected through resistor 42 to sensor 20, and terminal 3 being connected through resistor 44 to sensor 24. A resistor 48 is also connected across input terminals 2 and 3, and each terminal is protected by back-to-back Zener diode arrangements 50. A potentiometer 58 in series with a capacitor 60 is connected to terminals 5, 1 and 8 of the amplifier 40, and this is used to adjust the setting of the amplifier so that it can respond to the voltage level of each particular leaf.

The output of the operational amplifier 40, represented by terminal 6, is connected in a positive feedback arrangement to positive input terminal 3 through a resistor 64 and capacitor 68. The output terminal 6 is also connected through a resistor 70 to the base of NPN transistor 80 which has its output or collector connected to drive current through an iron core coil 90. The collector of transistor 80 is also provided with a jack or the like for connection to a chart recorder or the like.

System 10 also includes a permanent magnet 102 mounted in operative relation with the iron core of coil 90, and the magnet is secured to the clapper 104 of a wind bell assembly 106 having rod chimes or bells 110. The circuit is arranged so that, when current flows through the coil, the core thereof assumes a polarity which repels the permanent magnet 102.

System 10 includes both AC and battery power supply arrangements as shown and these are merely illustrative. Other arrangements could be used.

Figure 2:
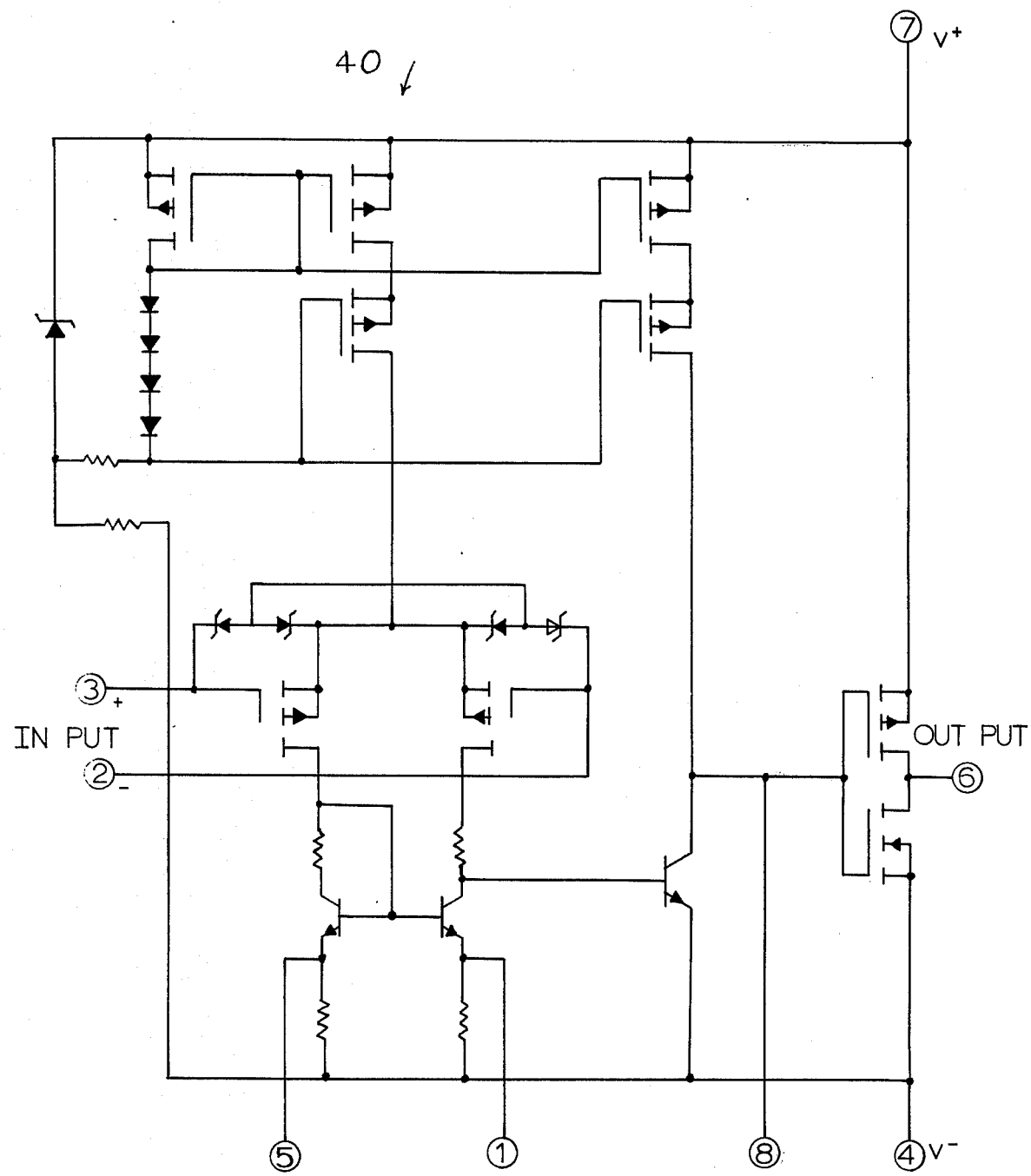
FIG. 2 is a schematic representation of the amplifier used in FIG. 1.

In operation of the system 10, the sensors 20 and 24 are clamped to a leaf 30 of a plant, and the reference probe 34 is inserted in the soil in which the plant is potted. The bias control potentiometer 58 is adjusted to set the amplifier 40 to respond to the voltage levels of the leaf and to cause the wind bells to ring. The plant leaf 30 exhibits generally continuous voltage changes of varying magnitude. Each voltage change is coupled into the input of amplifier 40, and, with the aid of positive feedback therein, drives the amplifier to saturation in one direction or the other (as can be seen in FIG. 2), and each such change provides current flow at the output of the amplifier. This current flow turns on transistor 80 and drives current through the coil 90 to polarize the iron core thereof to cause it to repel the magnet 102 and to thus cause the clapper 104 to ring the chimes 110. Each potential change in the leaf, of suitable magnitude, thus causes the chimes to ring.

The components of system 10, in one embodiment thereof, were as follows:

| | |
|---|---|
| Resistors 42 and 44 | 1 megohm |
| Resistor 48 | 22 megohms |
| Resistor 64 | 10 megohms |
| Resistor 58 | 100 Kohms |
| Resistor 70 | 10 Kohms |
| Capacitor 68 | .056 uf |
| Capacitor 60 | 100 pf |
| Capacitor C3 | 100 uf |
| Capacitor C4 | .1 uf |

The amplifier 40 has an input impedance of $1.5 \times 10^{12}$ ohms, and, as connected, it is sensitive to extremely small voltage changes at its input. In addition, both inputs are equal and balanced, and optimum common mode rejection is achieved. As arranged, the sensitivity level of the amplifier is about 100 uv.

The system is easy to handle and operate, and there is no damage to the leaves because of the use of the soft, mesh-like polyurethane sensors and because there is no significant current flow through the leaves in operation.

The iron core in coil 90 has an auxiliary advantage in that, when no current is flowing through the coil, the magnet attacts the iron core and thus provides a damping action on the clapper 102.

The small capacitor C1 used in the system combines with the high input impedance of the amplifier to provide a favorably long time constant.

Figure 3:
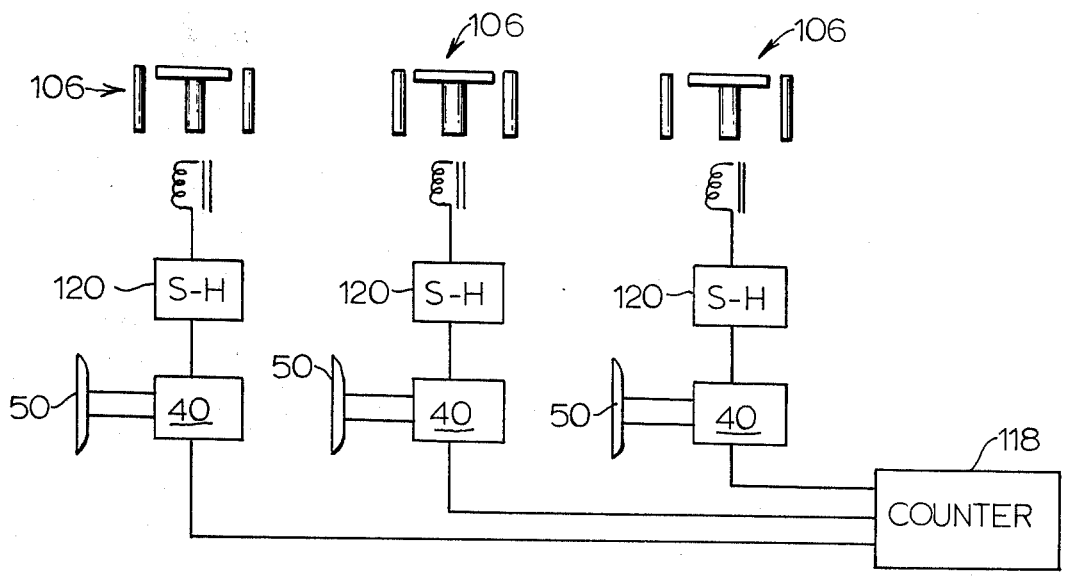
FIG. 3 is a schematic representation of a modification of the invention.

In a modification of the invention shown in FIG. 3, each leaf 50 of a plant is provided with a separate bell system. Each leaf is coupled to a separate amplifier 40 and the required associated circuitry, and a counter 118 is connected to each amplifier whereby each amplifier can be switched on separately and in turn to sense and display the potential of its leaf. The output of each amplifier is connected to its own wind chime apparatus 106 through a sample-and-hold circuit 120. As each amplifier is switched on, the potential of its leaf is sensed and reflected in ringing of its associated wind chimes or bells 106.

What is Claimed:

1. A plant voltage sensing system for sensing electrical potentials in the leaves of a plant comprising two conductive sensors capacitively coupled to opposite surfaces of a plant leaf whose electrical potential is to be sensed, a differential operational amplifier having high input impedance and having an
output and two inputs, each input being connected through a
resistive path to one of said sensors,
a resistive path connected across the two inputs of said amplifier, the output of said amplifier being coupled through a resistor and
capacitor to one input of said amplifier, both inputs of said amplifier also being connected through a Zener diode
arrangement to ground,
means connected to the output of said amplifier to receive current flow
therefrom in response to potential changes in said leaf and sensed by said sensors,
a utilization device for responding to said currentflow and providing
a useful representation thereof, and said utilization device comprising bell chimes that ring in response to said current changes whereby the changes in the plant potential of the plant causes said bell chimes to generate sound.

2. The system defined in claim 1 wherein said means includes an iron core coil, a permanent magnet in operative relation with said coil, said magnet and iron core repelling each other when current flows through said coil.

3. The system defined in claim 1 and including bias adjusting means for setting the operating level of said amplifier to respond to the voltage levels found in a particular body.

4. The system defined in claim 1 and including a positive feedback connection from the output to the input of said amplifier.

5. The system defined in claim 1 wherein said sensors comprise conductive polyurethane foam pads and said body comprises a plant leaf.

6. The system defined in claim 1 wherein said sensors comprise conductive polyurethane foam pads adapted to be clamped to said body.

* * * * *